US00PP11362P

United States Patent [19]

Kientzler

[11] Patent Number: Plant 11,362

[45] Date of Patent: Apr. 25, 2000

[54] NEW GUINEA IMPATIENS PLANT NAMED 'KIJOS'

[75] Inventor: Ludwig Kientzler, Gensingen, Germany

[73] Assignee: Paul Ecke Ranch, Inc., Encinitas, Calif.

[21] Appl. No.: 09/127,640

[22] Filed: Jul. 31, 1998

[51] Int. Cl.[7] ..... A01H 5/00

[52] U.S. Cl. ..... Plt./318

[58] Field of Search ..... Plt./318

[56] References Cited

U.S. PATENT DOCUMENTS

P.P. 7,789 2/1992 Drewlow ..... Plt./318

*Primary Examiner*—Howard J. Locker
*Assistant Examiner*—Kent L. Bell
*Attorney, Agent, or Firm*—C. A. Whealy

[57] ABSTRACT

A new and distinct cultivar of New Guinea Impatiens plant named 'Kijos', characterized by its numerous white-colored flowers that are held above the foliage; upright and outwardly spreading; broad "V"-shaped; uniform, rounded canopy; very freely branching, dense and bushy plant habit; and dark green leaves.

1 Drawing Sheet

BACKGROUND OF THE INVENTION

The present invention relates to a new and distinct cultivar of New Guinea Impatiens plant, botanically known as *Impatiens hawkeri*, and hereinafter referred to by the cultivar name 'Kijos'.

The new cultivar is a product of a planned breeding program conducted by the Inventor in Gensingen, Germany. The objective of the breeding program was to develop early-flowering varieties with numerous flowers, uniform plant habit, attractive flower and foliage colors, and good flower form.

The new cultivar originated from a cross made by the Inventor of the cultivar 'Moorea' (disclosed in U.S. Plant Pat. No. 9,147) as the male, or pollen parent, with the proprietary selection MF 302 as the female, or seed parent.

The cultivar 'Kijos' was discovered and selected by the Inventor as a flowering plant within the progeny of the stated cross in a controlled environment in Gensingen, Germany, in April, 1996.

Asexual reproduction of the new cultivar by terminal cuttings taken at Gensingen, Germany, has shown that the unique features of this new Impatiens are stable and reproduced true to type in successive generations of asexual reproduction.

SUMMARY OF THE INVENTION

The following traits have been repeatedly observed and are determined to be the unique characteristics of 'Kijos'. These characteristics in combination distinguish 'Kijos' as a new and distinct cultivar:

1. Numerous white-colored flowers that are held above the foliage.

2. Upright and outwardly spreading; broad "V"-shaped; uniform, rounded canopy.

3. Very freely branching, dense and bushy plant habit.

4. Dark green leaves.

Compared to plants of the female parent, the proprietary selection MF 302, plants of the new New Guinea Impatiens have larger flowers, larger leaves and more rounded flowers.

Plants of the new New Guinea Impatiens are similar in flower color to plants of the male parent, the cultivar 'Moorea'. However, in side-by-side comparisons conducted in Encinitas, Calif., plants of the new New Guinea Impatiens differed from plants of the cultivar 'Moorea' in the following characteristics:

1. Plants of the new New Guinea Impatiens are larger, more vigorous, have longer lateral branches, and are more spreading than plants of the cultivar 'Moorea'.

2. Plants of the new New Guinea Impatiens are more freely branching than plants of the cultivar 'Moorea'.

3. Leaves of plants of the new New Guinea Impatiens are longer and wider than leaves of plants of the cultivar 'Moorea'.

4. Flowers of plants of the new New Guinea Impatiens are held higher above the canopy and are angled more outwardly than flowers of plants of the cultivar 'Moorea'.

5. Flowers of plants of the new New Guinea Impatiens are slightly smaller and more rounded than flowers of plants of the cultivar 'Moorea'.

6. Plants of the new New Guinea Impatiens flower about 7 to 10 days earlier than plants of the cultivar 'Moorea'.

A detailed comparison of plants of the cultivars 'Kijos' and 'Moorea' appears in Chart A at the end of the specification.

Plants of the new New Guinea Impatiens are also similar in flower color to plants of the cultivar 'Jasius', disclosed in U.S. Plant Pat. No. 7,345. However, in side-by-side comparisons conducted in Gensingen, Germany, plants of the new New Guinea Impatiens were smaller; had broader, stiffer leaves; had more rounded flowers; and flowered about 10 to 14 days earlier than plants of the cultivar 'Jasius'.

BRIEF DESCRIPTION OF THE PHOTOGRAHPS

The accompanying colored photographs illustrate the overall appearance of the new cultivar, showing the colors as true as it is reasonably possible to obtain in colored reproductions of this type. The photograph at the top of the sheet comrpises a top perspective view of a typical plant of the cultivar 'Kijos'. The photograph at the bottom of the sheet comrpises a comparison close-up view of typical flowers and leaves of the cultivars 'Kijos' (left) and 'Moorea' (right).

Flower and foliage colors in the photographs may differ from the actual colors due to light reflectance.

DETAILED BOTANICAL DESCRIPTION

Plants of the cultivar 'Kijos' have not been observed under all possible environmental conditions. The phenotype may vary somewhat with variations in environment such as temperature and light intensity, without, however, any variance in genotype. The following observations, measurements and comparisons describe three plants measured separately in 25-cm hanging baskets in Encinitas, Calif., under commercial practice in a polyethylene- covered greenhouse with day temperatures ranging from 21 to 32° C. and night temperatures ranging from 16 to 18° C. and light levels of about 3,500 footcandles.

In the following description, color references are made to The Royal Horticultural Society Colour Chart except where general terms of ordinary dictionary significance are used.

Classification:

*Botanical.*—*Impatiens hawkeri* cultivar 'Kijos'.

*Commercial.*—New Guinea Impatiens cultivar 'Kijos'.

Parentage:

*Male parent.*—*Impatiens hawkeri* cultivar 'Moorea', disclosed in U.S. Plant Pat. No. 9,147.

*Female parent.*—Proprietary selection of *Impatiens hawkeri* identified as MF 302.

Propagation:

*Type cutting.*—Terminal cuttings.

*Time to initiate roots.*—Summer: About 14 days with 21° C. soil temperature. Winter: About 18 days with 21° C. soil temperature.

*Time to develop roots.*—Summer: About 21 days with 21° C. soil temperature. Winter: About 24 days with 21° C. soil temperature.

Plant description:

*Plant form.*—Upright and outwardly spreading; broad "V"-shaped; uniform, rounded canopy.

*Growth habit.*—Vigorous. Very freely branching, dense and bushy growth. Appropriate for 10 to 25-cm containers.

*Crop time.*—From planting of a rooted cutting, about six to eight weeks are required to produce a finished flowering plant in a 12.5-cm container.

*Plant size.*—Height: About 25 cm. Width or spread: About 41 cm.

*Lateral branches.*—Quantity: About 12. Length: About 20.5 cm. Diameter: About 1 cm. Internode length: About 4 cm. Color: 144A.

*Foliage description.*—Leaves simple, generally symmetrical, abundant, opposite or in whorls, horizontal to plant. Mostly flat. Length: About 10.25 cm. Width: About 4.4 cm. Shape: Elliptic with acuminate apex, attenuate base and serrulate margin with ciliation. Texture: Smooth, somewhat glossy. Color: Young foliage, upper surface: 137B. Young foliage, lower surface: 147C. Fully expanded foliage, upper surface: 147A. Fully expanded foliage, lower surface: 147C. Venation, upper surface: 147C. Venation, lower surface: 147D. Petiole: Length: About 3.75 cm. Diameter: About 3 mm. Color: 145B.

Flower description:

*Flower type and habit.*—White-colored flowers. Freely and continuously flowering. Flowers arise from leaf axils. Usually about 11 flowers and flower buds per lateral branch. Flowers positioned above the foliage and face upward and outward. Young flowers cupped but become flatter with development; flowers nearly rounded. Flowers persistent.

*Flowering season.*—Year-round under greenhouse conditions. In the garden, flowering is continuous from spring until fall. Flowers typically last less than one week depending on environmental and cultural conditions.

*Flower size.*—Length: About 5.5 cm. Width: About 5.5 cm. Depth: About 1.5 cm.

*Flower buds.*—Length: About 1.8 cm. Diameter: About 9 mm. Shape: Ovoid. Color: 157A.

*Petals.*—Quantity: Five. Length: Upper petal: About 3.7 cm. Middle petals: About 2.8 cm. Lower petals: About 3.5 cm. Width: Upper petal: About 4 cm. Middle petals: About 3.2 cm. Lower petals: About 3.7 cm. Shape: Cordate with acute base and entire margin. Texture: Velvety, smooth. Color: When opening, upper surface: 155D. When opening, lower surface: 155C. Fully opened, upper surface: 155C. Fully opened, lower surface: 155C.

*Spur.*—Length: About 5.2 cm. Shape: Narrow and curved. Color: 145D.

*Peduncles.*—Length: About 5.5 cm. Angle: Mostly outward. Strength: Strong. Color: 145C.

*Reproductive organs.*—Androecium: Stamen number: Five, anthers fused, filaments free. Anther shape: Obovate. Anther size: 3 mm by 4 mm. Anther color: 2D. Amount of pollen: Moderate. Pollen color: 155A. Gynoecium: Five-loculate fused. Pistil length: About 6 mm. Stigma color: 157A. Ovary color: 144A.

Disease resistance: Under commercial conditions, resistance to pathogens has not been observed.

Seed development: Seed production has not been observed.

CHART A

| CHARACTERISTIC | 'KIJOS' | 'MOOREA' |
|---|---|---|
| GROWTH HABIT, PLANT SHAPE | Upright, spreading, broad "V"-shape | Compact, rounded, mounding |
| PLANT HEIGHT | About 25 cm | About 21 cm |
| PLANT WIDTH | About 41 cm | About 29 cm |
| VIGOR | Vigorous | Moderate |
| NUMBER OF LATERAL BRANCHES | About 12 | About 7 |
| LATERAL BRANCH LENGTH | About 20.5 cm | About 16 cm |
| LATERAL BRANCH DIAMETER | About 1 cm | About 1.25 cm |
| INTERNODE LENGTH | About 4 cm | About 2.25 cm |
| LEAF LENGTH | About 10.25 cm | About 8.5 cm |
| LEAF WIDTH | About 4.4 cm | About 3.35 cm |
| PETIOLE LENGTH | About 3.75 cm | About 2.75 cm |
| FLOWER LOCATION | Above leaf canopy | At leaf canopy level |
| FLOWER SHAPE | Nearly round | Rounded oblong |
| FLOWER DIAMETER | About 5.5 by 5.5 cm | About 5.5 by 6 cm |
| PEDUNCLE ANGLE | Mostly outward | Upward |
| PEDUNCLE COLOR | 145C | 145A/145B |

It is claimed:

1. A new and distinct cultivar of New Guinea Impatiens plant named 'Kijos', as illustrated and described.

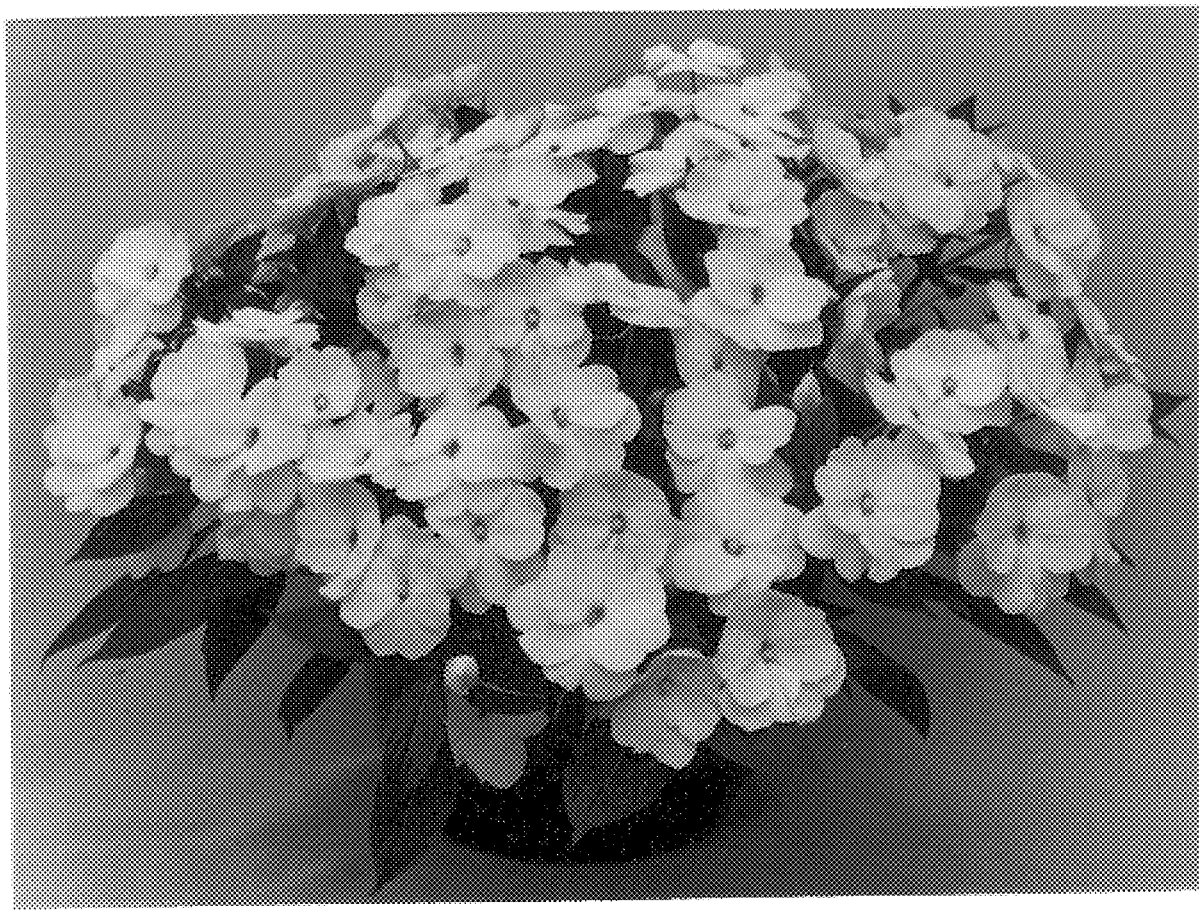
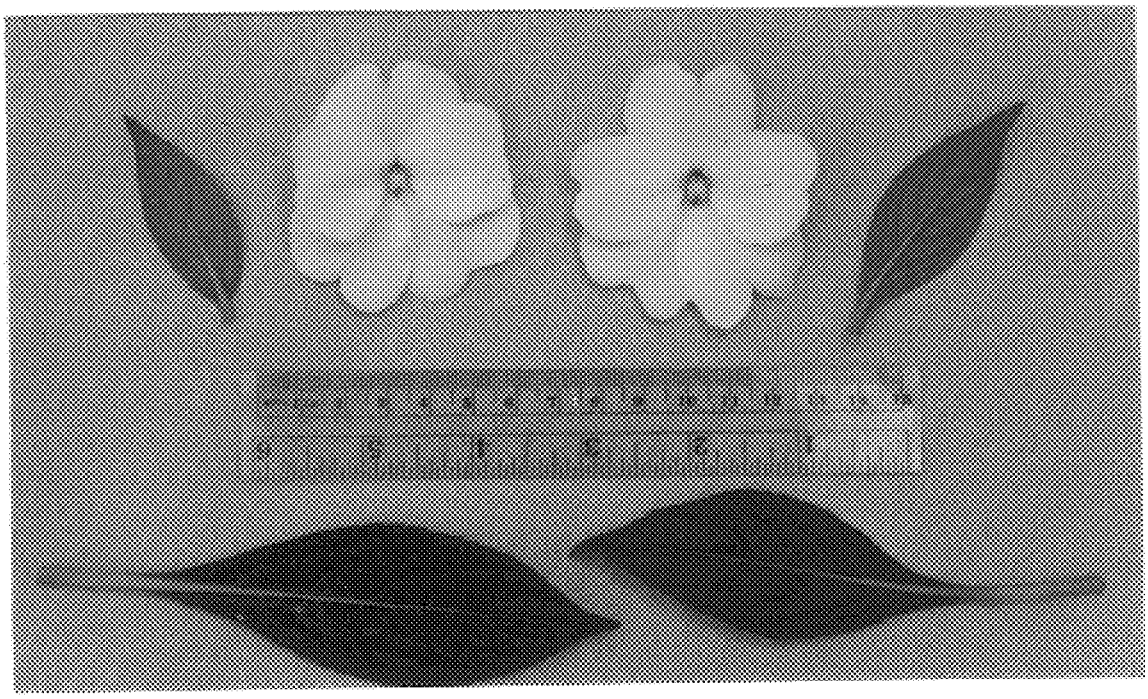

* * * * *